(12) United States Patent
De Rijke et al.

(10) Patent No.: US 10,369,492 B2
(45) Date of Patent: Aug. 6, 2019

(54) PROCESS FOR THE ISOLATION OF LEVULINIC ACID

(71) Applicant: GFBIOCHEMICALS IP ASSETS B.V., Geleen (NL)

(72) Inventors: Aris De Rijke, Geleen (NL); Rudy Francois Maria Jozef Parton, Geleen (NL); Donato Santoro, Valletta (MT)

(73) Assignee: GFBIOCHEMICALS IP ASSETS B.V., Geleen (NL)

( * ) Notice: Subject to any disclaimer, the term of this patent is extended or adjusted under 35 U.S.C. 154(b) by 18 days.

(21) Appl. No.: 15/743,115

(22) PCT Filed: Jul. 8, 2016

(86) PCT No.: PCT/EP2016/066250
§ 371 (c)(1),
(2) Date: Jan. 9, 2018

(87) PCT Pub. No.: WO2017/009221
PCT Pub. Date: Jan. 19, 2017

(65) Prior Publication Data
US 2019/0099691 A1    Apr. 4, 2019

(30) Foreign Application Priority Data
Jul. 10, 2015 (EP) .................................. 15176315

(51) Int. Cl.
*C07C 51/44* (2006.01)
*B01D 3/00* (2006.01)
*B01D 1/26* (2006.01)
*C07C 59/185* (2006.01)

(52) U.S. Cl.
CPC .............. *B01D 3/009* (2013.01); *B01D 1/26* (2013.01); *C07C 51/44* (2013.01); *B01D 2257/70* (2013.01); *C07C 59/185* (2013.01)

(58) Field of Classification Search
CPC ...... B01D 3/009; B01D 1/26; B01D 2257/70; C07C 51/44; C07C 59/185
See application file for complete search history.

(56) References Cited

U.S. PATENT DOCUMENTS

| | | | |
|---|---|---|---|
| 3,065,263 A * | 11/1962 | Carlson ............... | C07C 51/00 562/515 |
| 4,236,021 A | 11/1980 | Hsu et al. | |
| 4,897,497 A | 1/1990 | Fitzpatrick | |
| 5,189,215 A | 2/1993 | Farnleitner et al. | |
| 5,608,105 A | 3/1997 | Fitzpatrick | |
| 6,054,611 A | 4/2000 | Farone et al. | |
| 2010/0312006 A1 | 12/2010 | Lake et al. | |
| 2012/0215026 A1 | 8/2012 | Tolan et al. | |

FOREIGN PATENT DOCUMENTS

| | | |
|---|---|---|
| CN | 201445816 U | 5/2010 |
| CN | 201492956 U | 6/2010 |
| CN | 203355317 U | 12/2013 |
| CN | 203425540 U | 2/2014 |
| CN | 203507566 U | 4/2014 |
| WO | 2010030617 A1 | 3/2010 |
| WO | 2010138957 A1 | 12/2010 |
| WO | 2014189991 A1 | 11/2014 |

\* cited by examiner

*Primary Examiner* — Yevgeny Valenrod
*Assistant Examiner* — Blaine G Doletski
(74) *Attorney, Agent, or Firm* — Hudak, Shunk & Farine Co. LPA

(57) ABSTRACT

A process for the isolation of levulinic acid obtained by acid catalyzed hydrolysis of a C6-carbohydrate-containing feedstock, including the following steps: a) providing a solution 1 comprising at least 5 wt. % of levulinic acid, at least 0.1 wt. % of formic acid and at most 94.9 wt. % of solvent, relative to the total weight of solution 1, b) feeding solution 1 to a first evaporation step to treat solution 1 and to obtain solution 2, comprising at least 25 wt. % of levulinic acid, less than 20 wt. % of solvent and at least 1 wt. % of formic acid, relative to the total weight of solution 2, c) feeding solution 2 to a second evaporation step to treat solution 2 and to obtain solution 3, comprising at least 30 wt. % of levulinic acid and less than 1.0 wt. % of formic acid, relative to the total weight of solution 3, d) feeding solution 3 to a third evaporation step to treat solution 3 and to obtain levulinic acid with a purity of at least 90 wt. % and containing less than 1000 wppm angelica lactone.

15 Claims, 1 Drawing Sheet

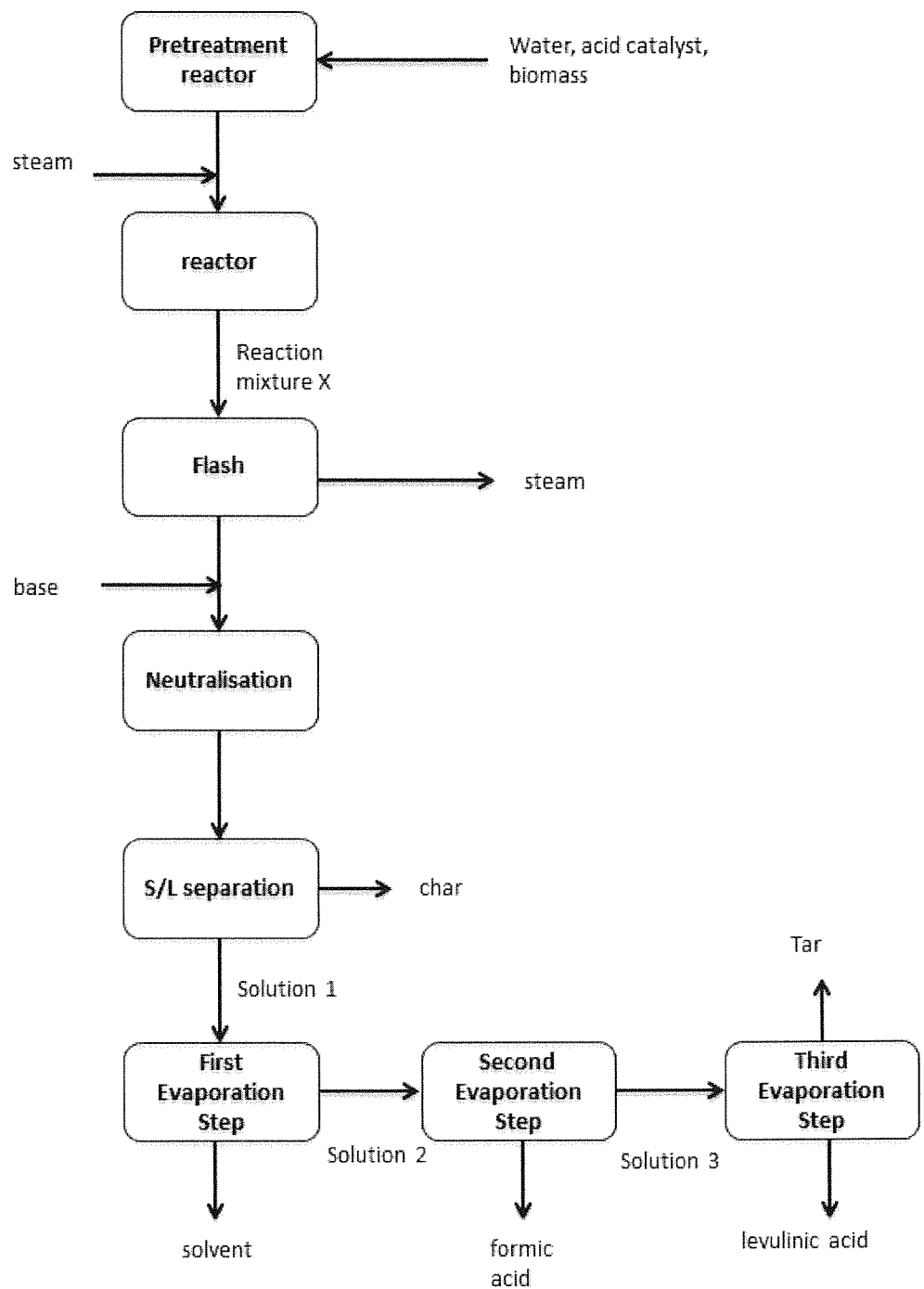

PROCESS FOR THE ISOLATION OF LEVULINIC ACID

FIELD OF THE INVENTION

The present invention is directed to a process for the isolation of levulinic acid. Levulinic acid, or 4-oxopentanoic acid, is an organic compound with the formula $CH_3C(O)CH_2CH_2CO_2H$. It can be obtained by degradation of cellulose that is for example present in agricultural waste products, waste from the paper industry or municipal waste. Levulinic acid is a precursor to pharmaceuticals, plasticizers, and various other additives. Also biofuels such as methyltetrahydrofuran, gamma-valerolactone, and ethyl levulinate can be prepared from levulinic acid.

BACKGROUND OF THE INVENTION

In the prior art several processes for the production of levulinic acid are described. Levulinic acid can, for example, be produced by acid catalyzed hydrolysis of C6 carbohydrate-containing feedstocks. The production of levulinic acid by acid catalyzed hydrolysis of C6 carbohydrate-containing feedstocks is described e.g. in WO2010/030617, US2010/312006, U.S. Pat. Nos. 5,608,105, 4,897,497 and 6,054,611.

Another process for the production of levulinic acid is a process that produces levulinic acid from furfuryl alcohol or its esters. An example of such a process is described in U.S. Pat. No. 4,236,021. Furfurylalcohol is converted at 125° C. to butyl levulinate in the presence of an alcohol, such as butylalcohol, with HCl as catalyst. Butyl levulinate is isolated via distillation. After hydrolysis in an aqueous environment levulinic acid is obtained.

A third process for the production of levulinic acid is from diethyl acetyl succinate as, for example, described in U.S. Pat. No. 5,189,215. Diethyl acetyl succinate can be made from diethyl maleate, which in general is derived from petrochemical based maleic acid anhydride.

In the present invention levulinic acid is produced by acid catalyzed hydrolysis of a C6 carbohydrate-containing feedstock. During acid catalyzed hydrolysis a solution is formed comprising levulinic acid and by-products (e.g. char, tar and angelica lactone) and a solvent.

The formation of char, tar and angelica lactone is a serious disadvantage of the production of levulinic acid by acid catalyzed hydrolysis. Char contains insoluble compounds which can be removed via traditional solid liquid separation steps such as decanting, filtering and other solid liquid separation technologies. Tar is composed of low to high-molecular weight oligomeric and polymeric compounds and other high boiling compounds. Tar can be soluble and/or partly insoluble. In particular tar forms a problem during the isolation of levulinic acid, for example during a distillation step. Liquid-liquid extraction is used in many processes according to the prior art. During the extraction of levulinic acid from the aqueous phase also a part of the tar is extracted. During distillation, that is needed for further purification, the remaining tar may accumulate in the distillation residue and forms a sticky, almost solid layer which is difficult to remove from the distillation column. The tar will foul reboilers and column internals and will make it very difficult to recover levulinic acid. The recovery of levulinic acid by distillation moreover often requires high temperatures and long residence times. Under these process conditions angelica lactone is formed via internal cyclisation and dehydration of levulinic acid.

Angelica lactone is the cyclic dehydration product of levulinic acid. It is also called 4-hydroxy-3-pentenoic acid γ-lactone or 5-methyl-2(3H)-furanone. Angelica lactone has a lower boiling point than levulinic acid and, thus will accumulate in the distilled levulinic acid fraction after removal of the tar. Angelica lactone may form colored compounds in the distilled levulinic acid fraction.

Here and hereafter, reaction product X is herewith defined as the reaction product that is directly obtained after the acid catalyzed hydrolysis of a C6 carbohydrate-containing feedstock.

SUMMARY OF THE INVENTION

The object of the invention is to provide a process that makes it possible to obtain a substantially pure levulinic acid, in particular levulinic acid with a low amount of angelica lactone.

The inventors surprisingly discovered that with the following process for the isolation of levulinic acid obtained by acid catalyzed hydrolysis of a C6-carbohydrate-containing feedstock, a levulinic acid can be obtained with a purity of at least 90 wt. % and containing less than 1000 wppm angelica lactone.

The process according to the invention comprises the following steps: a) providing a solution 1 comprising at least 5 wt. % of levulinic acid, at least 0.1 wt. % of formic acid and at most 94.9 wt. % of solvent, relative to the total weight of solution 1, b) feeding solution 1 to a first evaporation step to treat solution 1 and to obtain solution 2, comprising at least 25 wt. % levulinic acid, less than 20 wt. % of solvent and at least 1 wt. % of formic acid, relative to the total weight of solution 2, c) feeding solution 2 to a second evaporation step to treat solution 2 and to obtain solution 3, comprising at least 30 wt. % levulinic acid and less than 1.0 wt. % of formic acid, relative to the total weight of solution 3, d) feeding solution 3 to a third evaporation step to treat solution 3 and to obtain levulinic acid with a purity of at least 90 wt. % and containing less than 1000 wwppm angelica lactone.

The high purity of the levulinic acid obtained by this process was a real surprise.

During the acid catalyzed hydrolysis of a C6 carbohydrate-containing feedstock many by-products are formed, comprising monomers, dimers, oligomers and polymers, that form the char and the tar in the reaction solution. These by-products preferably are separated from the levulinic acid in the reaction product X to obtain a substantially pure levulinic acid. According to the prior art liquid-liquid extraction is often employed to separate at least a part of the by-products from the levulinic acid. The solvent containing the levulinic acid is thereafter treated by distillation to obtain a substantially pure levulinic acid. A man skilled in the art knows from the prior art that distillation units with a large number of plates are required to remove the by-products. For example, in WO2010/030617, par. 31, a distillation column containing 40 trays is described. The skilled person would not expect that the use of evaporation instead of distillation would allow the desired purification as is known that the separation that can be obtained in an evaporator is normally about the same as a separation that can be obtained between two plates in a distillation column. Therefore, it is surprising that with the process according to the invention comprising three evaporation steps in series, wherein the three evaporation steps can comprise in total three to eight evaporators, levulinic acid is obtained with a purity of at least 90 wt. % and containing less than 1000 wppm angelica lactone.

An evaporation step is a unit operation which can consist of more than one evaporator; an evaporator is defined as the physical apparatus to perform such a unit operation.

As used herein, 'distillation' or 'rectification' is intended to mean multi stage evaporating, condensing and recovering.

As used herein, 'evaporation' means single stage evaporating, condensing and recovering. 'Evaporation' does not include 'distillation' or 'rectification'.

Here and hereafter the wording 'substantially pure levulinic acid' is defined as a levulinic acid with a purity of at least 90 wt. %.

Here and hereafter wppm is the abbreviation of 'weight parts per million'.

An advantage of the process according to the invention is that no liquid-liquid extraction needs to be performed before feeding the solution of levulinic acid to the evaporators. Preferably, a reaction product X, that is obtained by acid catalyzed hydrolysis of a C6 carbohydrate-containing feedstock, is concentrated to a solution wherein levulinic acid is present in an amount of at least 5 wt. %, formic acid in an amount of at least 0.1 wt. % and solvent in an amount of at most 94.9 wt. %, This is an advantage because liquid-liquid extraction is an, expensive and time-consuming, extra step in the purification of a reaction product X and also because no organic solvent needs to be used in the isolation process. Moreover, even traces of the organic solvent preferably are removed from the waste stream to prevent environmental issues.

Another advantage is that the process according to the invention can be performed as a continuous process.

A further advantage is that levulinic acid can be obtained in a high yield.

A further advantage is that in the evaporators almost no angelica lactone is formed.

Reaction product X is the solution that leaves the reactor wherein the acid catalyzed hydrolysis of a C6-carbohydrate-containing feedstock is performed.

The process for the isolation of levulinic acid starts with the provision of a solution 1, comprising at least 5 wt. % of levulinic acid, at least 0.1 wt % of formic acid and at most 94.9 wt. % of solvent, that is obtained by acid catalyzed hydrolysis of a C6-carbohydrate-containing feedstock.

A C6-carbohydrate is a compound consisting of carbon (C), hydrogen (H) and oxygen (O) atoms. In its monomeric form it comprises 6 carbon atoms and has a hydrogen atom:oxygen atom ratio of 2:1.

A C6-carbohydrate-containing feedstock is for example a feedstock comprising monosaccharides, such as fructose and glucose; disaccharides such as saccharose and lactose and polysaccharides such as starch and cellulose. A C6-carbohydrate-containing feedstock is also a lignocellulosic feedstock, which comprises cellulose, hemicellulose and lignin. Examples of lignocellulosic feedstocks are wood; wood processing side products such as saw dust, wood chippings and wood shavings; grass; cereals, algae; tree bark; hay; straw; leaves and paper pulp. Paper pulp, or simply pulp, is a lignocellulosic fibrous material prepared by chemically or mechanically separating cellulose from wood, fibrous crops or waste paper. The feedstock is treated by acid catalyzed hydrolysis. Various acid catalysts are suitable for use during acid catalyzed hydrolysis. These include, but are not limited to, inorganic acids such as sulfuric acid, fluorosulfonic acid, hydrochloric acid, nitric acid, phosphoric acid, benzenesulfonic acid, phosphotungstic acid, phosphomolybdic acid; organic acids such as p-toluene sulfonic acid, trifluoromethanesulfonic acid, 1,1,2,2-tetrafluoroethanesulfonic acid, 1,1,2,3,3,3-hexafluoropropanesulfonic acid, and mixtures thereof; acidic ion exchange resins; Brönsted acid catalysts such as bismuth triflate, yttrium triflate, ytterbium triflate, neodymium triflate, lanthanum triflate, scandium triflate, zirconium triflate, and $Zn(BF_4)_2$; fluorinated sulfonic acid polymers; metal salts of acid such as metal sulfonates, metal sulfates, metal trifluoroacetates, metal triflates; heteropolyacids; and perfluoroalkylsulfonic acids.

After the acid catalyzed hydrolysis the reaction product X can be neutralized by a base before further treatment takes place.

The C6-carbohydrates in the raw material are catalytically converted during acid catalyzed hydrolysis to substantially C5 levulinic acid and C1 formic acid.

Filtration or centrifugation is typically used to separate the desired solution of levulinic acid from the char by-products. Filtration can be performed after the reactor to remove the solid char and/or salts from the reaction product X. Further, the reaction product X of levulinic acid can be pretreated, for example by distillation, solvent extraction and evaporation, for example flash evaporation, to obtain a solution 1 comprising at least 5 wt. % of levulinic acid, at least 0.1 wt. % of formic acid and at most 94.9 wt. % of solvent, relative to the total weight of solution 1.

In solution 1 the levulinic acid is present in an amount of at least 5 wt. %, preferably at least 6 wt. %, more preferably at least 8 wt. %, most preferably at least 10 wt. % relative to the total weight of solution 1.

In solution 1 the levulinic acid is present in an amount of at most 60 wt. %, preferably at most 50 wt. %, more preferably at most 40 wt. %, most preferably at most 30 wt. %.

In solution 1 formic acid is present. Formic acid is a by-product that is formed during the production of levulinic acid by acid catalyzed hydrolysis of C6-containing carbohydrates. Formic acid is present in solution 1 in an amount of at least 0.1 wt. %, preferably at least 0.5 wt. % of formic acid, more preferably at least 1 wt. % of formic acid.

In solution 1 there is no upper limit for the amount of formic acid; the amount of formic acid is preferably as high as possible, but the amount of formic acid will not exceed 95 wt. %.

The solvent in the solution can be water, an organic solvent or mixtures thereof. Examples of suitable organic solvents are methyltetrahydrofuran (MTHF), methyl isoamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxy-phenol, methylene chloride, methyl isobutyl carbinol, anisol, ethylene glycol di-n-butyl ether, diethyl carbonate, methyl salicylate, methyl levulinate, ethyl levulinate, toluene, methyl-tertiary butyl ether, hexane, cyclohexane, chloro-benzene, dichloroethane, ortho-dichlorobenzene, 2,6-dimethyl cyclohexanone, tetrahydrofuran, furfural and mixtures thereof.

According to a preferred embodiment of the invention no liquid-liquid extraction needs to be performed to obtain solution 1. When no liquid-liquid extraction is performed before obtaining solution 1, solution 1 is an aqueous solution. Therefore, preferably the solvent is water.

In solution 1 the solvent is present in an amount of at most 94.9 wt. % of solvent, preferably at most 92 wt. % of solvent, more preferably at most 90 wt. % of solvent relative to the total weight of solution 1.

In solution 1 the solvent can be present in an amount of at least 50 wt. %, preferably at least 40 wt. %, more preferably at least 30 wt. %, most preferably at least 25 wt. % relative to the total weight of solution 1.

According to step b, c and d of the invention a solution of levulinic acid is fed to an isolation section, wherein three evaporation steps in series are performed.

The evaporation steps in the isolation section can be performed in a total of three to eight evaporators, preferably in three to six evaporators. Each evaporation step comprises at least one evaporator.

The solutions comprising levulinic acid are treated during an evaporation step. By treating the solution is meant that the solution is fed into an evaporator and heated.

An evaporator is a device that is used to turn the liquid form of a chemical or solvent into its vapor form. By heat the liquid in the solution is vaporized. The vapor or part of the vapor is removed from the remaining solution and is condensed. Heating the solutions comprising levulinic acid can be performed at atmospheric pressure or at reduced pressure. Preferably, the solutions comprising levulinic acid are treated at reduced pressure.

By treating solutions comprising levulinic acid solvent and/or impurities can be removed from the solutions.

The process of evaporation is widely used to concentrate solutions of chemicals. In the concentration process, the aim of evaporation in step b is to vaporize most of the water and/or other solvents from a solution which contains the desired product. In the chemical industry, the evaporation process is used to eliminate excess moisture, providing a product and improving product stability. Heat is added to the solution, and part of the solvent is converted into vapor. Heat is the main driving force in evaporation, and the evaporation process occurs more readily at higher temperature and lower pressure. Heat is needed to provide enough energy for the molecules of the solvent to leave the solution and move into the vapor phase. Heat can be provided by various sources that can be in direct or indirect contact with the solution containing the desired product. Examples for heating sources that are in indirect contact with the solution are heating coils or a heating mantle. In the heating coils or heating mantle a heating medium is present that provides the heat. The heating medium can also be in direct contact with the solution. Examples of heating media are steam or any other hot liquid or gaseous stream.

Evaporators can be classified into four different categories:
- Evaporators in which a heating medium is not in direct contact with the evaporating liquid by tubular heating surfaces.
- Evaporators in which a heating medium is confined by coils, jackets, double walls etc.
- Evaporators in which a heating medium is brought into direct contact with the evaporating fluid.
- Evaporators in which heating is done with solar radiation.

The evaporator or evaporators in the evaporation steps can be chosen from the group of kettle evaporators, internal reboilers, thermo-syphon evaporators, plate and frame heat exchangers, spiral wound heat exchangers, shell and tube heat exchangers, forced circulation evaporators, falling film evaporators, rising film evaporators or agitated thin film evaporators.

Preferably, the evaporator or evaporators in the evaporation steps is/are operated at a liquid temperature between 100 and 200° C. The liquid temperature is preferably higher than 110° C., more preferably higher than 120° C. The liquid temperature is preferably lower than 190° C., more preferably lower than 180° C.

According to step b of the invention solution 1 is fed to a first evaporation step to treat solution 1 and to obtain solution 2, comprising at least 25 wt. % levulinic acid, less than 20 wt. % of solvent and at least 1 wt. % of formic acid, relative to the total weight of solution 2.

Preferably, the amount of levulinic acid in solution 2 is at least 30 wt. %, more preferably at least 35 wt. %.

Preferably, the amount of solvent in solution 2 is less than 10 wt. %, more preferably less than 5 wt. %, relative to the total weight of solution 2.

Preferably, the amount of formic acid in solution 2 is at least 1 wt. %, preferably at least 2 wt. %, more preferably at least 5 wt. %, relative to the total weight of solution 2.

Preferably, the evaporator or evaporators in step B is/are operated at a pressure between 5-500 kPa. The pressure is more preferably higher than 10 kPa, most preferably higher than 20 kPa. The pressure is more preferably lower than 400 kPa, most preferably lower than 300 kPa.

Step b can be performed in 1 evaporator or in 2 to 4 evaporators provided that solution 2 is obtained having less than 20 wt. % of solvent and at least 1 wt. % of formic acid, relative to the total weight of solution 2.

The evaporator or evaporators for step b is/are preferably chosen from a kettle evaporator, a forced circulation evaporator, a falling film evaporator, a rising film evaporator or an agitated thin film evaporator. Preferably, at least one of the evaporators in first evaporation step is a forced circulation evaporator.

According to step c of the process according to the invention solution 2 is fed to a second evaporation step to treat solution 2 and to obtain solution 3, comprising at least 30 wt. % levulinic acid and less than 1.0 wt. % formic acid based on the total weight of solution 3.

Preferably, solution 3 comprises at least 35 wt. % of levulinic acid, more preferably more than 40 wt. % of levulinic acid.

Preferably, in the second evaporation step (step c) a solution 3 is obtained having less than 0.8 wt. % formic acid, more preferably less than 0.5 wt. % formic acid.

Preferably, the evaporator or evaporators in step c are operated at a pressure between 1-20 kPa. The pressure is preferably higher than 2 kPa, more preferably higher than 3 kPa.

The pressure is preferably lower than 15 kPa, more preferably lower than 9 kPa.

Step c can be performed in one or two evaporators provided that solution 3 is obtained that is having less than 1 wt. % formic acid relative to the total weight of solution 3. Preferably, one evaporator is used to perform step c.

The evaporators for step care preferably chosen from a forced circulation evaporator or an agitated thin film evaporator.

Preferably, at least one of the evaporators in the second evaporation step is an agitated thin film evaporator.

According to step d of the process according to the invention solution 3 is fed to a third evaporation step to treat solution 3 and to obtain levulinic acid with a purity of at least 80 wt. %. Preferably, the purity is at least 85 wt. %, more preferably at least 90 wt. %, most preferably at least 95 wt. %, in particular at least 99 wt. %.

Preferably, the evaporator or evaporators in step d are operated at a pressure between 0.1-7.5 kPa.

The pressure is preferably higher than 0.2 kPa, more preferably higher than 0.3 kPa.

The pressure is preferably lower than 7 kPa, more preferably lower than 2 kPa.

Step d can be performed in one or two evaporators provided that levulinic acid is obtained with a purity of at least 90 wt. %. Preferably, one evaporator is used to perform step d.

Preferably, at least one evaporator in the third evaporation step is an agitated thin film evaporator. An agitated thin film evaporator sometimes also called thin film dryer or agitated thin film dryer is an evaporator which typically consists of a tubular heat transfer area with an external heating jacket and a fast-revolving, inner rotor with flexible or rigid wiper elements. The driving speed of the rotor is adapted to the product being handled. The function of the rotor is to spread the product evenly over the inner surface of the heated wall, and generate a highly turbulent flow condition in the thin layer of the liquid. The advantage of using an agitated thin film evaporator is that in an agitated thin film evaporator solutions with a high viscosity can be handled and purified.

The agitated thin film evaporator can be a vertical agitated thin film evaporator and a horizontal agitated thin film evaporator or a spray dryer. Preferably, the agitated thin film evaporator is a vertical agitated thin film evaporator.

The levulinic acid that is obtained in the process according to the invention contains less than 1000 wppm angelica lactone, preferably less than 100 wppm angelica lactone, more preferably less than 50 wppm angelica lactone, most preferably less than 20 wppm angelica lactone, in particular less than 10 wppm angelica lactone.

According to an embodiment of the invention one evaporator is present in each evaporation step and the evaporator in the first evaporation step is a forced circulation evaporator, the evaporator in the second evaporation step is a first agitated thin film evaporator and the evaporator in the third evaporation step is a second agitated thin film evaporator.

The isolation process according to the invention can be a continuous, semi-continuous or a batch process. Preferably, the isolation process according to the invention is a continuous process.

According to a preferred embodiment the isolation process according to the invention comprises the following steps: a) providing a levulinic acid-containing reaction product X by acid catalyzed hydrolysis of a C6-carbohydrate-containing feedstock and purifying reaction product X to obtain solution 1, comprising at least 5 wt. % of levulinic acid, at least 0.1 wt. % of formic acid and at most 94.9 wt. % of solvent, relative to the total weight of solution 1, wherein during purification of reaction product X no liquid-liquid extraction is used, b) feeding solution 1 to a first evaporation step to treat solution 1 and to obtain solution 2, comprising at least 25 wt. % of levulinic acid, less than 20 wt. % of solvent and at least 1 wt. % of formic acid, relative to the total weight of solution 2, c) feeding solution 2 to a second evaporation step to treat solution 2 and to obtain solution 3, comprising at least 30 wt. % of levulinic acid and less than 1.0 wt. % of formic acid, relative to the total weight of solution 3, d) feeding solution 3 to a third evaporation step to treat solution 3 and to obtain levulinic acid with a purity of at least 90 wt. % and containing less than 1000 wppm angelica lactone.

According to a further preferred embodiment the isolation process according to the invention comprises the following steps: a) providing a levulinic acid-containing reaction product X by acid catalyzed hydrolysis of a C6-carbohydrate-containing feedstock and purifying reaction product X to obtain solution 1, comprising at least 5 wt. % of levulinic acid, at least 0.1 wt. % of formic acid and at most 94.9 wt. % of solvent, relative to the total weight of solution 1, wherein during purification of product X no liquid-liquid extraction is used, b) feeding solution 1 to a forced circulation evaporator to treat solution 1 and to obtain solution 2, comprising at least 25 wt. % of levulinic acid, less than 20 wt. % of solvent and at least 1 wt. % of formic acid, relative to the total weight of solution 2, wherein the forced circulation evaporator is operated at a pressure between 5-500 kPa and at a liquid temperature between 100 and 200° C., c) feeding solution 2 to a second agitated thin film evaporator to treat solution 2 and to obtain solution 3, comprising at least 30 wt. % of levulinic acid and less than 1.0 wt. % of formic acid, relative to the total weight of solution 3, wherein the second agitated thin film evaporator is operated at a pressure between 1-20 kPa and at a liquid temperature between 100 and 200° C., d) feeding solution 3 to an agitated thin film evaporator to treat solution 3 and to obtain levulinic acid with a purity of at least 90 wt. % and containing less than 1000 wppm angelica lactone, wherein the agitated thin film evaporator is operated at a pressure between 0.1-7.5 kPa and at a liquid temperature between 100 and 200° C.

As described above for the process according to the invention the process comprises three evaporation steps. In these three evaporation steps in total three to eight evaporators can be used. Preferably, three to six evaporators are used.

The invention is also directed to an isolation section in a plant for the production of levulinic acid comprising three to eight evaporators in series.

BRIEF DESCRIPTION OF THE DRAWING

In The FIGURE a scheme of a plant according to one embodiment of the invention is shown.

DETAILED DESCRIPTION OF THE INVENTION

In the plant according to The FIGURE a continuous process for the production of levulinic acid can be performed.

According to The FIGURE water, C6 carbohydrate-containing feedstock and an acid catalyst are mixed in a pretreatment reactor. The obtained mixture is fed to a reactor. The reaction mixture is brought to the desired temperature and pressure by steam. After the required reaction time the reaction product leaves the reactor and the pressure is reduced to atmospheric pressure in a flash tank. Steam is removed from the flash tank. Thereafter, the reaction mixture is neutralized by the addition of a base and a solid/liquid separation takes place to remove char. Solution 1 is obtained after solid/liquid separation.

Thereafter, solution 1 is fed to an isolation section formed by a series of three evaporation steps to obtain levulinic acid. During the first evaporation step solvent is removed and solution 2 is formed. Solution 2 is fed to the second evaporation step. During the second evaporation step formic acid is removed and solution 3 is formed. Solution 3 is fed to the third evaporation step. During the third evaporation step tar is removed and levulinic acid is obtained as the final product.

The isolation section in a plant according to the invention preferably comprises at least one agitated thin film evaporator.

More preferably, the isolation section in a plant according to the invention comprises a succession of a forced circulation evaporator, a first agitated thin film evaporator and a second agitated thin film evaporator.

The invention is further directed to the use of three to eight evaporators in series for the isolation of levulinic acid from a solution of levulinic acid, comprising at least 5 wt. % of levulinic acid, at most 0.1 wt. % of formic acid and at most 94.9 wt. % of solvent relative to the total weight of solution 1, obtained by acid catalyzed hydrolysis of a C6-carbohydrate-containing feedstock.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

Example

A pretreatment reactor was conditioned by adding 5 tons of water. Thereafter, water was fed with a flow of 2500 kg/h at a temperature of about 90° C. and the other ingredients were fed as well. Dry corn with a flow of 500 kg/h and HCl 32% (Chimpex Industriale) with a flow of 250 kg/h. The total mixture was homogeneously mixed in the pretreatment reactor. The slurry contained about 2.6 wt. % HCl and 15 wt. % corn and the total flow was 3250 kg/h. The mixture was pumped to the reactor and heated with 1300 kg/h steam of 17 bar (210° C.) up to 12 bar (185° C.). The total flow became 4550 kg/h. The residence time in the reactor was 1 hour. The stream leaving the reactor contained levulinic acid (LA) 150 kg/h, formic acid (FA) 50 kg/h, solid char 120 kg/h, tar 140 kg/h and intermediate boiling solubles 10 kg/h. Intermediate boiling solubles are compounds with a boiling point between the boiling point of levulinic acid and the boiling point of formic acid.

The solution leaving the reactor was flashed in a flash tank to atmospheric pressure hereby venting the steam (1300 kg/h) that was needed to heat the reactor. The slurry was partially neutralized (to a pH of 3) with 300 kg/h soda 30% (Chimpex Industriale, 90 kg/h soda absolute) and the total flow became 3550 kg/h. During the neutralization water was made as well as salt (130 kg/h). The slurry was filtered and char was separated with a moisture content of about 42 wt %. The total char removal was about 210 kg/h. Therefore the final flow was 3340 kg/h. The process was continued for 5.8 hours until a total amount of slurry of 19372 kg was made. Together with the 5 initial tons of water this made about 24400 kg that contained 850 kg of LA (3.4 wt. %), 260 of FA (1.1 wt. %), 740 kg (3 wt. %) of salt and 850 kg (3.4 wt. %) of tar and intermediate soluble boilers.

A part of total slurry (10.7 tons) was concentrated in a horizontal evaporator heated by thermal oil in a heat exchanger. The temperature of the thermal oil in the evaporator gradually increased from 140° C. until 180° C. was reached. In the same period the pressure was reduced from 100 kPa to 50 kPa. In the final portion of the evaporator the salts precipitated and were removed and the final solution had a total mass of 3.6 ton containing 360 kg LA (10 wt. %), 108 kg FA (3 wt. %), 360 kg tar and intermediate boilers (10 wt. %) and 180 kg salts (5 wt. %).

From this solution levulinic acid was recovered via a series of thin film evaporators.

In a first Forced Circulated Evaporator the major amount of water was removed. The evaporator was operated with a liquid temperature of 150° C. and a pressure of 15 kPa. 125 kg/h of the final solution mentioned above was split in a top stream (91.95 kg/h) and a bottom stream (33.05 kg/h) in the evaporator. The top stream contained 0.125 kg/h LA (0.14 wt. %), 3.48 kg/h FA (3.8 wt. %), and 88.35 kg/h water (96.1 wt. %). The bottom stream had 12.38 kg/h LA (37.4 wt. %), 0.28 kg/h FA (0.8 wt. %), 1.65 kg/h water (5 wt. %), 6.25 kg/h salts (18.9 wt. %) and 12.5 kg/g tar and intermediate boilers (37.8 wt. %).

The lights of this bottom stream were removed in an agitated thin film evaporator. The evaporator was operated with a bottom temperature of 150° C. and at a pressure of 3 kPa. The top stream contained 9 wt. % LA (0.17 kg/h), 8 wt. % FA (0.15 kg/h), 75 wt. % water (1.41 kg/h) and 8 wt. % intermediate boilers (0.15 kg/h). The total mass flow was 1.88 kg/h. The bottom stream had a size of 31.17 kg/h and contained 39.2 wt. % LA (12.2 kg/h), 0.4 wt. % FA (0.125 kg/h), 0.8 wt. % water (0.24 kg/h) and 39.6 wt. % tar and intermediate boilers (12.34 kg/h) and 18.9 wt. % salts (6.25 kg/h).

The levulinic acid in the viscous bottom stream was recovered in an agitated thin film evaporator. The evaporator was operated with a liquid temperature of 150° C. and at a pressure of 1 kPa. The top stream contained 90.7 wt. % LA (11.66 kg/h), 0.4 wt. % FA (0.05 kg/h), 1.9 wt. % water (0.24 kg/h) and 7 wt. % intermediate boilers (12.35 kg/h). The total mass flow was 12.85 kg/h. The bottom stream had a size of 18.32 kg/h and contained 3 wt. % LA (0.55 kg/h), 0.4 wt. % FA (0.07 kg/h), 62.5 wt. % tar (11.45 kg/h) and 18.9 wt. % salts (6.25 kg/h). That gave a recovery of levulinic acid over the series of film evaporators of 93.2 wt. %. It was unexpected and surprising that via these three evaporators in series such a high recovery and purity (above 90%) could be obtained, certainly seen the high viscosity of the feed and the broad range of boiling points of the tar and intermediate boiling compounds. Moreover it was surprising that in none of the top streams angelica lactone could be detected.

What is claimed is:

1. A process for the isolation of levulinic acid obtained by acid catalyzed hydrolysis of a C6-carbohydrate-containing feedstock, comprising the following steps:
    a) providing a solution 1 comprising at least 5 wt. % of levulinic acid, at least 0.1 wt. % of formic acid and at most 94.9 wt % of solvent, relative to the total weight of solution 1,
    b) feeding solution 1 to a first evaporation step to treat solution 1 and to obtain solution 2, comprising at least 25 wt. % of levulinic acid, less than 20 wt. % of solvent and at least 1 wt. % of formic acid, relative to the total weight of solution 2,
    c) feeding solution 2 to a second evaporation step to treat solution 2 and to obtain solution 3, comprising at least 30 wt. % of levulinic acid and less than 1.0 wt. % of formic acid the total weight of solution 3,
    d) feeding solution 3 to a third evaporation step to treat solution 3 and to obtain levulinic acid with a purity of at least 90 wt. % and containing less than 1000 wppm angelica lactone.

2. The process according to claim 1, wherein each of steps c and d is performed in 1 evaporator or 2 evaporators.

3. The process according to claim 1, wherein the evaporator or evaporators in the evaporation steps are operated at a liquid temperature between 100 and 200° C.

4. The process according to claim 1, wherein the evaporator or evaporators in step b are operated at a pressure between 5-500 kPa.

5. The process according to claim 1, wherein the evaporator or evaporators in step c are operated at a pressure between 1-20 kPa.

6. The process according to claim 1, wherein the evaporator or evaporators in step d are operated at a pressure between 0.1-7.5 kPa.

7. The process according to claim 1, wherein one evaporator is present in each evaporation step and the evaporator in the first evaporation step is a forced circulation evaporator, the evaporator in the second evaporation step is a first agitated film evaporator and the evaporator in the third evaporation step is a second agitated thin film evaporator.

8. The process according to claim 1, wherein levulinic acid in solution 1 is present in an amount of at least 10 wt. %, relative to the total weight of solution 1.

9. The process according to claim 1, wherein the isolation process is a continuous process.

10. The process according to claim 1, wherein the solvent is water.

11. The process according to claim 1, wherein in solution 1 the levulinic acid is present in an amount of at most 60 wt. %.

12. The process according to claim 1, wherein during purification of reaction product X in step a no liquid-liquid extraction is used.

13. The process according to claim 12, wherein
a) solution 1 is fed to a forced circulation operated at a pressure between 5-500 kPa and at a liquid temperature between 100 and 200° C.,
b) solution 2 is fed to a first agitated thin film evaporator operated at a pressure between 1-20 kPa and at a liquid temperature between 100 and 200° C. and
c) solution 3 is fed to a second agitated thin film evaporator operated at a pressure between 0.1-7.5 kPa and at a liquid temperature between 100 and 200° C.

14. The process according to claim 3, wherein the evaporator or evaporators in step b are operated at a pressure between 5-500 kPa, wherein the evaporator or evaporators in step c are operated at a pressure between 1-20 kPa, wherein the evaporator or evaporators in step d are operated at a pressure between 0.1-7.5 kPa, and wherein one evaporator is present in each evaporation step and the evaporator in the first evaporation step is a forced circulation evaporator, the evaporator in the second evaporation step is a first agitated film evaporator and the evaporator in the third evaporation step is a second agitated thin film evaporator.

15. The process according to claim 14, wherein levulinic acid in solution 1 is present in an amount of at least 10 wt. %, relative to the total weight of solution 1, wherein the isolation process is a continuous process, wherein the solvent is water, wherein in solution 1 the levulinic acid is present in an amount of at most 60 wt. %, and wherein during purification of reaction product X in step a no liquid-liquid extraction is used.

* * * * *